(12) United States Patent
Sabol et al.

(10) Patent No.: US 7,270,890 B2
(45) Date of Patent: Sep. 18, 2007

(54) WEAR MONITORING SYSTEM WITH EMBEDDED CONDUCTORS

(75) Inventors: Stephen M. Sabol, Orlando, FL (US); Ramesh Subramanian, Oviedo, FL (US)

(73) Assignee: Siemens Power Generation, Inc., Orlando, FL (US)

( * ) Notice: Subject to any disclaimer, the term of this patent is extended or adjusted under 35 U.S.C. 154(b) by 212 days.

(21) Appl. No.: 11/018,816

(22) Filed: Dec. 20, 2004

(65) Prior Publication Data
US 2005/0158511 A1    Jul. 21, 2005

Related U.S. Application Data

(63) Continuation-in-part of application No. 10/252,236, filed on Sep. 23, 2002, now Pat. No. 6,838,157.

(51) Int. Cl.
*B32B 9/00* (2006.01)

(52) U.S. Cl. ............... 428/632; 428/469; 428/701; 428/702; 416/61; 73/7

(58) Field of Classification Search ............ None
See application file for complete search history.

(56) References Cited

U.S. PATENT DOCUMENTS

| | | | |
|---|---|---|---|
| 2,888,023 A * | 5/1959 | Eggenberger | ............ 415/14 |
| 3,800,278 A | 3/1974 | Jaye et al. | |
| 3,876,998 A | 4/1975 | Richter et al. | |
| 3,890,456 A | 6/1975 | Dils | |
| 3,897,116 A * | 7/1975 | Carpenter | ............ 384/297 |
| 3,981,621 A | 9/1976 | Considine | |
| 4,016,533 A | 4/1977 | Ishikawa et al. | |
| 4,188,613 A | 2/1980 | Yang et al. | |
| 4,384,819 A | 5/1983 | Baker | |
| 4,390,870 A * | 6/1983 | Michael | ............ 340/648 |
| 4,536,670 A | 8/1985 | Mayer | |
| 4,578,992 A | 4/1986 | Galasko et al. | |
| 4,595,298 A | 6/1986 | Frederick | |

(Continued)

OTHER PUBLICATIONS

Sensors for Harsh Environments by Direct Write Thermal Spray. By Jon, Longtin, et al. Center for Thermal Spray Research, State University of New York, Stony Brook, NY, and Robert Greenlaw. Integrated Coatings Solutions, Inc., Huntington Beach, CA.

(Continued)

*Primary Examiner*—Jennifer McNeil
*Assistant Examiner*—Timothy M. Speer

(57) ABSTRACT

Aspects of the invention relate to a system for monitoring the wear of a component. A conductor can be embedded in the component at a depth from a surface of the component. In one embodiment, the conductor can be operatively connected to a power source to form an electrical circuit. The resistance across the conductor can be measured. As the component contacts a second component, the component can begin to wear. Once the wear progresses to the conductor, changes in the measured resistance can result. Thus, an operator can be alerted that the component has worn to a certain point and that service may be needed. Alternatively, impedance can be measured across the conductor. Because the dielectric permeability of the material surrounding the conductor can affect impedance, changes in impedance can occur as the surface material of the component is worn away.

16 Claims, 8 Drawing Sheets

U.S. PATENT DOCUMENTS

| | | | |
|---|---|---|---|
| 4,642,557 A * | 2/1987 | Ross | 324/71.2 |
| 4,774,150 A | 9/1988 | Amano et al. | |
| 4,812,050 A | 3/1989 | Epstein et al. | |
| 4,851,300 A | 7/1989 | Przybyszewski | |
| 4,916,715 A | 4/1990 | Adiutori | |
| 4,983,034 A | 1/1991 | Spillman, Jr. | |
| 5,144,299 A | 9/1992 | Smith | |
| 5,248,940 A | 9/1993 | Patience et al. | |
| 5,440,300 A | 8/1995 | Spillman, Jr. | |
| 5,632,359 A | 5/1997 | Camps et al. | |
| 5,701,119 A * | 12/1997 | Jurras, III | 340/682 |
| 5,818,242 A | 10/1998 | Grzybowski et al. | |
| 6,000,977 A | 12/1999 | Haake | |
| 6,142,665 A | 11/2000 | Haffner et al. | |
| 6,197,424 B1 | 3/2001 | Morrison et al. | |
| 6,251,978 B1 | 6/2001 | McCullough | |
| 6,260,004 B1 | 7/2001 | Hays et al. | |
| 6,398,503 B1 | 6/2002 | Takahashi et al. | |
| 6,434,512 B1 | 8/2002 | Discenzo | |
| 6,437,681 B1 | 8/2002 | Wang et al. | |
| 6,512,379 B2 | 1/2003 | Harrold et al. | |
| 6,580,511 B1 | 6/2003 | Discenzo | |
| 6,644,917 B2 | 11/2003 | Zhao et al. | |
| 6,730,918 B2 | 5/2004 | Srivastava et al. | |
| 2003/0011388 A1 | 1/2003 | Klaar | |
| 2003/0115941 A1 | 6/2003 | Srivastava et al. | |
| 2003/0126928 A1 | 7/2003 | Harrold et al. | |
| 2003/0127602 A1 | 7/2003 | Harrold et al. | |
| 2003/0193331 A1 | 10/2003 | Nath et al. | |
| 2003/0202188 A1 | 10/2003 | Discenzso | |
| 2004/0096314 A1 | 5/2004 | Kool et al. | |
| 2004/0101022 A1 | 5/2004 | Hardwicke et al. | |
| 2004/0114666 A1 | 6/2004 | Hardwicke et al. | |

OTHER PUBLICATIONS

Laser-Induced Materials And Processes for Rapid Prototyping. By L. Lu, et al. Chapter 6: Metal-Based System Via Laser Melting. The National University of Singapore. Boston, Kluwer Academic Publishers.

Direct-Write Technologies for Rapid Prototyping Applications: Sensors, Electronics, and Integrated Power Sources. Chapter 9: Direct-Write Thermal Spraying of Multilayer Electronics and Sensor Structures, by Sansay Sampath, et al. pp. 261-302. San Diego, CA: Academic Press.

* cited by examiner

WEAR MONITORING SYSTEM WITH EMBEDDED CONDUCTORS

CROSS-REFERENCE TO RELATED APPLICATIONS

This application is a Continuation-In-Part of U.S. patent application Ser. No. 10/252,236 filed Sep. 23, 2002 now U.S. Pat. No. 6,838,157.

FIELD OF THE INVENTION

The invention relates in general to component wear and, more particularly, to systems for monitoring component wear.

BACKGROUND OF THE INVENTION

In many applications, there can be two or more components in contact. Relative motion between such components can result in excessive wear of the components. Such component wear can ultimately affect the proper functioning of the components and the system or assembly of which they are a part.

Wear can be controlled within acceptable levels in some instances by the use of lubricants, by material selection and/or by design features that limit the motion and/or geometry of the components. However, there are many instances in which relative motion cannot be eliminated, such as in brake linings, gears, sliders and slip fits; wear is unavoidable in such cases. The extent of the wear and the suitability of the component for continued service are typically determined by visual and/or dimensional inspection. In some applications, wear indicators have been developed. For example, in the context of brake linings, wear limit notches or "squealers" can provide an audible warning that a certain amount of wear has occurred.

However, there are many applications in which regular inspection is not feasible because of a number of factors including, for example, time, labor, cost and disruptions due to down time. Thus, there is a need for a system that can monitor the wear of a component while the component is in operation or without having to remove the component from its operational position.

SUMMARY OF THE INVENTION

Aspects of the invention relate to a wear monitoring system. One wear monitoring system according to aspects of the invention includes a first component and a second component. In one embodiment, the first component can be a gas turbine engine component. The first component has a surface. A first conductor is embedded in the first component at a predetermined depth beneath the surface. In one embodiment, the first component can include a base material on which there is one or more layers of a coating thereon. In such case, the first conductor can be embedded within the coating.

A power source is operatively connected to provide current to the first conductor. Thus, an electrical circuit is formed. A measurement device is operatively positioned to measure an electrical value across at least a portion of the first conductor. The electrical value can be one of resistance, current, voltage and impedance.

The second component contacts the surface of the first component such that at least the surface of the first component wears. As a result, a user can monitor the measurement device for changes in the measured electrical value indicating that the wear has progressed at least to the predetermined depth.

In one embodiment, there can be a second conductor embedded in the first component at a predetermined depth beneath the surface. The second conductor can be operatively connected to receive current from the power source. The measurement device can be operatively positioned to measure the electrical value across at least a portion of the second conductor. The first and second conductors can be electrically insulated from each other and can be separately operatively connected to the power source. In such case, two isolated circuits can be formed. In one embodiment, the first and second conductors can be electrically connected in parallel.

The first and second conductors can be provided in the first component at substantially the same depth beneath the surface of the first component. Alternatively, the first and second conductors can be provided in the first component at different depths beneath the surface of the first component. In such case, the first conductor and the second conductor can provide at least partially overlapping areas of coverage about the first component.

Another wear monitoring system according to aspects of the invention includes a first component and a second component. The first component has a first surface. The first component can be a gas turbine engine component. A first conductor is embedded in the first component at a predetermined depth beneath the first surface. In one embodiment, the first component can include a base material on which there is one or more layers of a coating. In such case, the first conductor can be embedded within the coating. The second component has a second surface; at least a portion of the second surface of the second component is conductive.

A power source is operatively connected to the first conductor and to the conductive surface of the second component. Thus, an initially open circuit is formed. The second surface and the first surface are in contact such that at least the first surface wears. Eventually, the first surface becomes sufficiently worn such that the second surface contacts the first conductor. Such contact completes the circuit, which can alert a user that the wear has progressed to at least the predetermined depth.

The system can further include a measurement device operatively positioned to measure resistance, current, voltage and/or impedance across at least a portion of the first conductor and the conductive surface of the second component. Thus, changes in the measured resistance, current, voltage and/or impedance can indicate that a predetermined amount of wear has occurred.

In one embodiment, a second conductor can be embedded in the first component at a predetermined depth beneath the first surface. The second conductor can be operatively connected to receive current from the power source such that an initially open circuit is formed. Thus, when the first surface is sufficiently worn such that the second surface contacts the second conductor, the circuit can be completed. The completion of the circuit can alert a user that the wear has progressed to at least the predetermined depth at which the second conductor is located.

The first and second conductors can be electrically insulated from each other and can be separately operatively connected to the power source. As a result, two isolated initially open circuits can be formed. In one embodiment, the first and second conductors can be electrically connected in parallel.

The first and second conductors can be provided in the first component at substantially the same depth beneath the first surface of the first component. Alternatively, the first and second conductors can be provided in the first component at different depths beneath the first surface of the first component. In such case, the first conductor and the second conductor can provide at least partially overlapping areas of coverage about the first component.

DETAILED DESCRIPTION OF EMBODIMENTS OF THE INVENTION

Embodiments of the present invention provide a system that can monitor the wear of a component. Embodiments of the invention will be explained in the context of various possible wear monitoring systems, but the detailed description is intended only as exemplary. Embodiments of the invention are shown in FIGS. 1-8, but the present invention is not limited to the illustrated structure or application.

Figure 1:
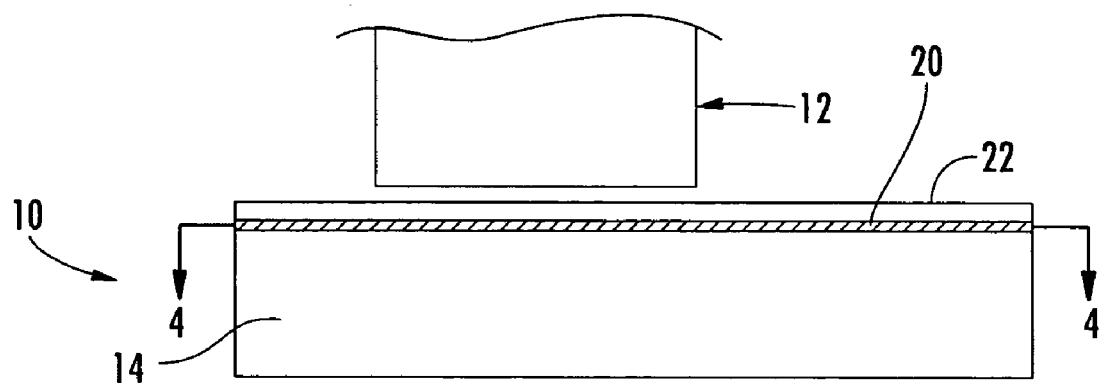
FIG. 1 is a cross-sectional elevational view of a component having a wear conductor embedded therein according to aspects of the invention, showing the wear conductor embedded in the base material of the component.

Referring to FIG. 1, a system according to aspects of the invention generally involves monitoring the wear of a component 10. While in use, the component 10 can contact another component 12, such as in sliding relation. Such contact may be substantially constant, periodic or irregular. The contact between the components 10, 12 can be an intentional or necessary part of the design, or the contact may be an unintentional consequence of an operational condition, such as vibration.

Because aspects of the invention have broad application, the component 10 can be almost any component of a system or assembly. However, aspects of the invention are particularly beneficial in cases where regular inspection of the component 10 for wear is not feasible, such as when the component 10 is not readily viewable or removable for visual, dimensional or borsescopic inspection or some other intrusive inspection technique. A system according to aspects of the invention is also ideal for instances in which the expense of inspecting the component 10 exceeds the cost of completely replacing the component 10.

As noted, aspects of the invention can be used in a variety of applications. For instance, aspects of the invention used in the context of turbine engines. Several components in a turbine engine are well suited for monitoring according to aspects of the invention including, for example, compressor diaphragms, seal holders on stationary airfoils, ring segment attachments, transition duct seals, thermocouple tubes, and airfoils having abradable and/or thermal barrier coatings. Each of these components can contact other components during engine operation. For example, during certain operating conditions, the tip of a turbine airfoil can come into contact with an abradable coating on a blade ring or other stationary structure in the turbine. Thus, aspects of the invention can be used to monitor the wear of the abradable coating. Again, the field of turbine engines is only one of many applications in which aspects of the invention can be used.

The component 10 can include a base material 14, which can be any of a number of materials including, for example, metals, ceramics, ceramic matrix composites, plastics, composites. It may be necessary or desirable to protect the base material 14 of the component 10 from an external environment. To that end, a coating 16 can be applied on a surface 18 of the component 10. The coating 16 can provide at least one of thermal insulation, environmental isolation and wear resistance. The coating 16 can be, for example, a wear resistant coating, a thermal barrier coating or an environmental barrier coating. The coating 18 can be applied as a single layer or in more than one layer. In some instances, a bond coat (not shown) can be deposited on the surface 18 of the component 10 prior to the application of the coating 16. The bond coat can improve adherence of the coating 16 to the surface 18.

Figure 2:
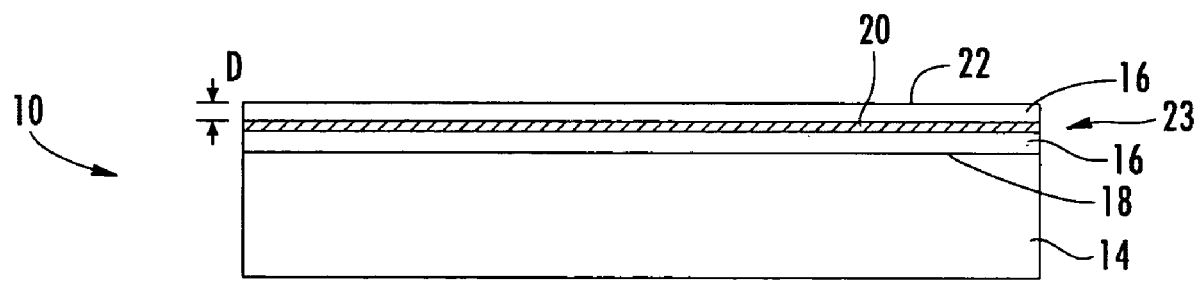
FIG. 2 is a cross-sectional elevational view of a component having a wear conductor embedded therein according to aspects of the invention, showing the wear conductor embedded in a coating material applied on the base material of the component.

According to aspects of the invention, at least one wear conductor 20 can be embedded below an exposed surface 22 of the component 10, as shown in FIG. 1. The adjective "wear" associated with the conductors 20 is merely for convenience to distinguish over other conductors that may be described herein; the term "wear" is not intended to limit the scope of the invention in any way. Further, it will be understood that the phrase "embedded in the component" means that the wear conductors 20 can be embedded in the base material 14 of the component 10 (as shown in FIG. 1), in the coating 16 applied on the component 10 (as shown in FIG. 2), in the bond coat, or in any of interfaces between the base material 14, the coating 16 and the bond coat. Regardless of the exact location of the wear conductors 20, the surface of the substrate on which they are provided can be substantially flat, or it can be curved or otherwise irregular. Accordingly, the wear conductors 20 can follow the contour of the substrate on which they are provided.

As shown in FIG. 2, the wear conductors 20 can be provided at a desired depth D from the exposed surface 22 of the component 10. For example, the wear conductors 14 can be placed a critical depth where repair or replacement of the component 10 or the coating 16 is required. The wear conductors 20 can be embedded within the component 10 so as to extend substantially about the entire component 10 or just in a local area of the component 10 where wear is known or suspected to occur.

Figure 4A:
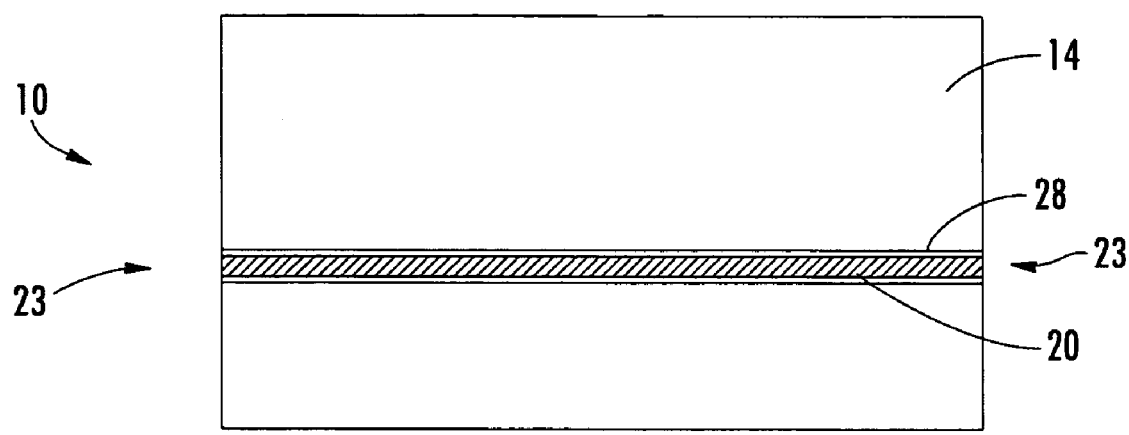
FIG. 4A is a cross-sectional view of a first arrangement of a single wear conductor in the component according to aspects of the invention, viewed from line 4-4 in FIG. 1.
Figure 4B:
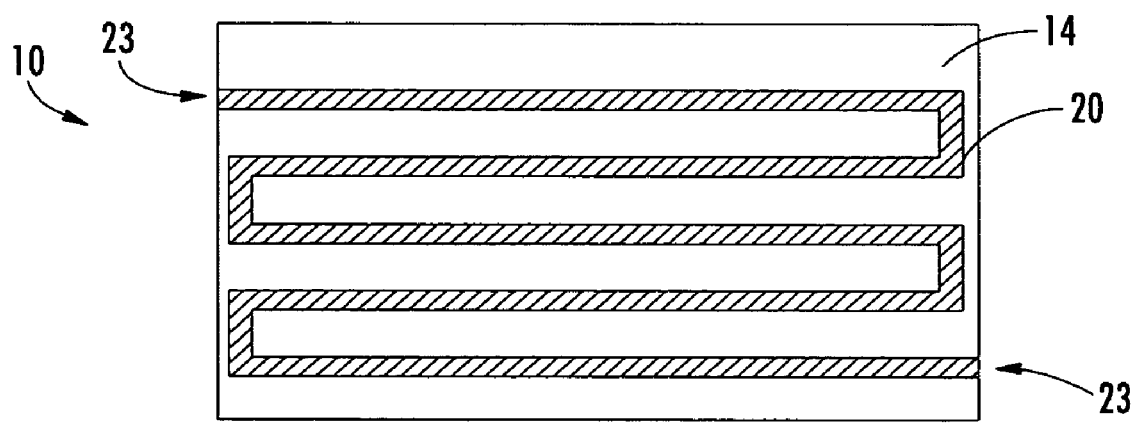
FIG. 4B is a cross-sectional view of a second arrangement of a single wear conductor in the component according to aspects of the invention, viewed from line 4-4 in FIG. 1.
Figure 4C:
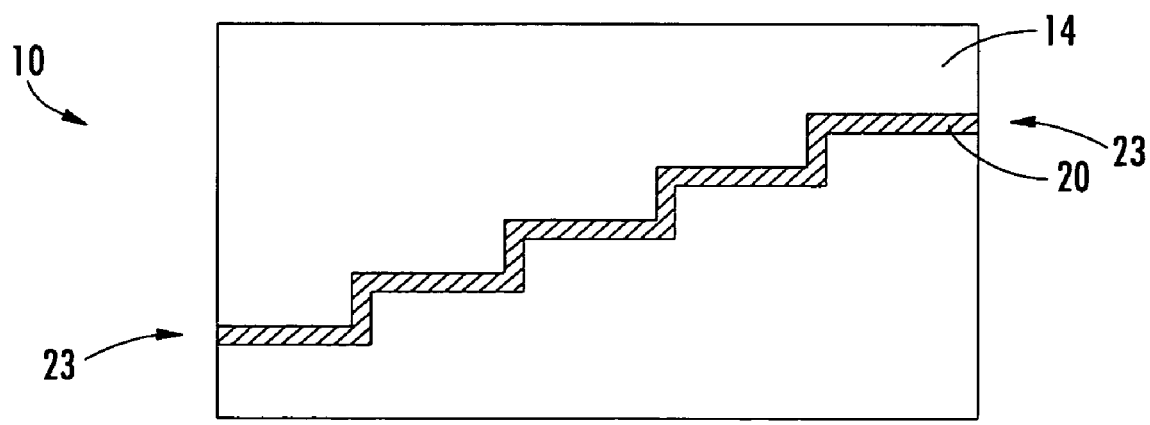
FIG. 4C is a cross-sectional view of a third arrangement of a single wear conductor in the component according to aspects of the invention, viewed from line 4-4 in FIG. 1.
Figure 4D:
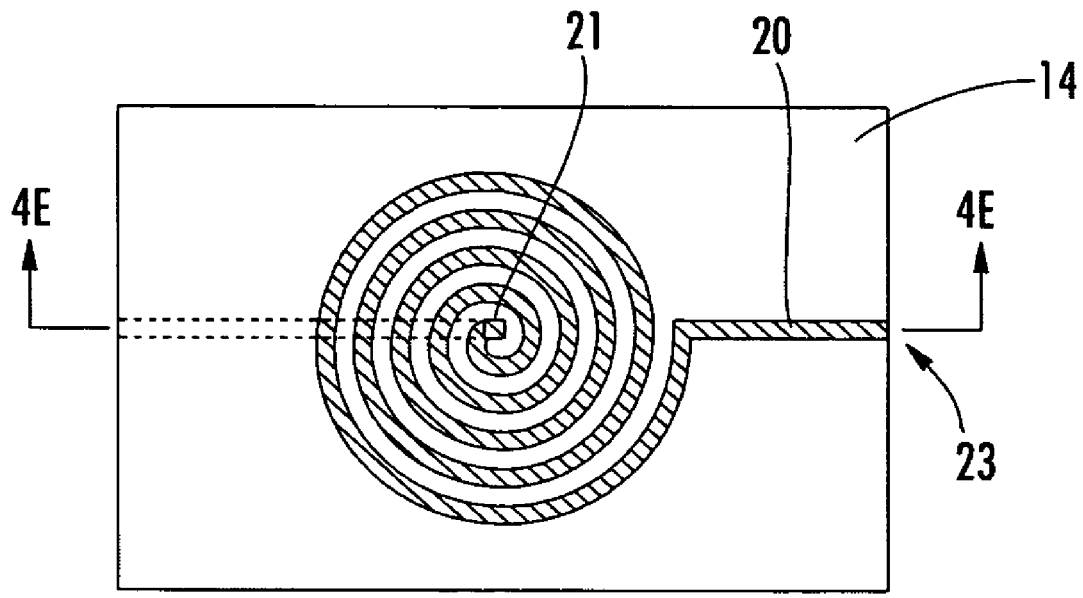
FIG. 4D is a cross-sectional view of a fourth arrangement of a single wear conductor in the component according to aspects of the invention.
Figure 4E:
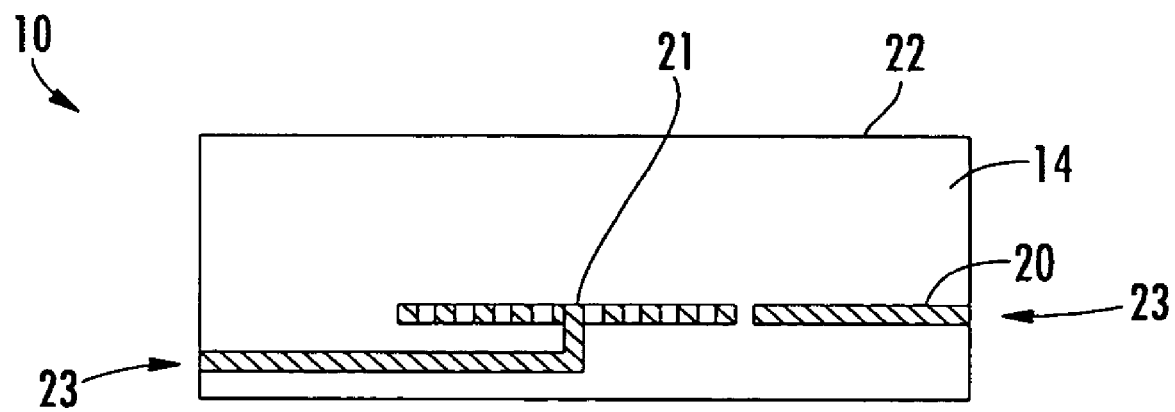
FIG. 4E is a cross-sectional view of the fourth arrangement of a single wear conductor in the component according to aspects of the invention, viewed from line 4E-4E in FIG. 4D.

There can be any quantity of wear conductors 20. In one embodiment, there can be a single wear conductor 20. In such case, the single wear conductor 20 can be arranged in a variety of ways. For example, as shown in FIG. 4A, the wear conductor 20 can be substantially straight. However, the wear conductor 20 can routed as needed to avoid features provided on the component 10. In one embodiment, the wear conductor 20 can be provided in a substantially serpentine arrangement, such as in a U-shaped pattern (as shown in FIG. 4B), a stepped pattern (as shown in FIG. 4C) or in a coiled pattern (as shown in FIGS. 4D and 4E).

It should be noted that the single wear conductor 20 can be substantially at one depth from the surface 22 of the component 10. However, in some cases, it may be necessary or desirable to provide the wear conductor 20 at more than one depth in the component 10 or on more than one layer of a multi-layer coating. For example, in the case of the coiled arrangement of FIGS. 4D and 4E, the wear conductor 20, once it reaches the center 21 of the coil, can extend upward or downward (as shown) away therefrom and laterally extend to a connection location 23 where it can exit the component 10.

Figure 4F:
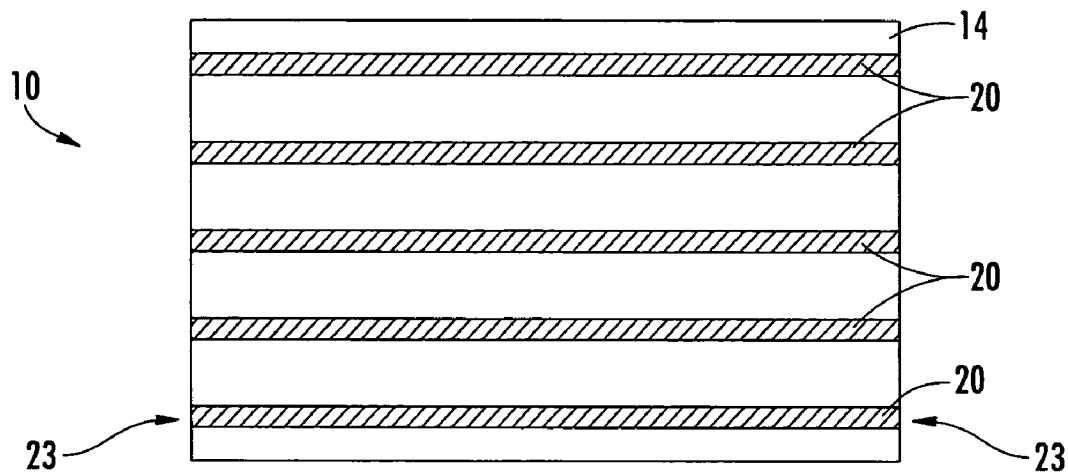
FIG. 4F is a cross-sectional view of a first arrangement of a plurality of wear conductors in the component according to aspects of the invention, viewed from line 4-4 in FIG. 1.
Figure 4G:
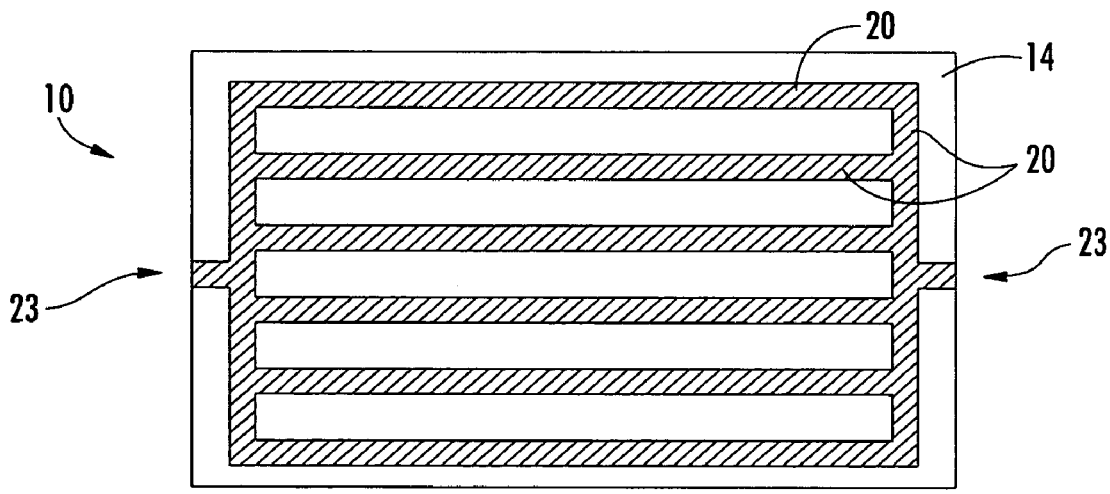
FIG. 4G is a cross-sectional view of a second arrangement of a plurality of wear conductors in the component according to aspects of the invention, viewed from line 4-4 in FIG. 1.
Figure 4H:
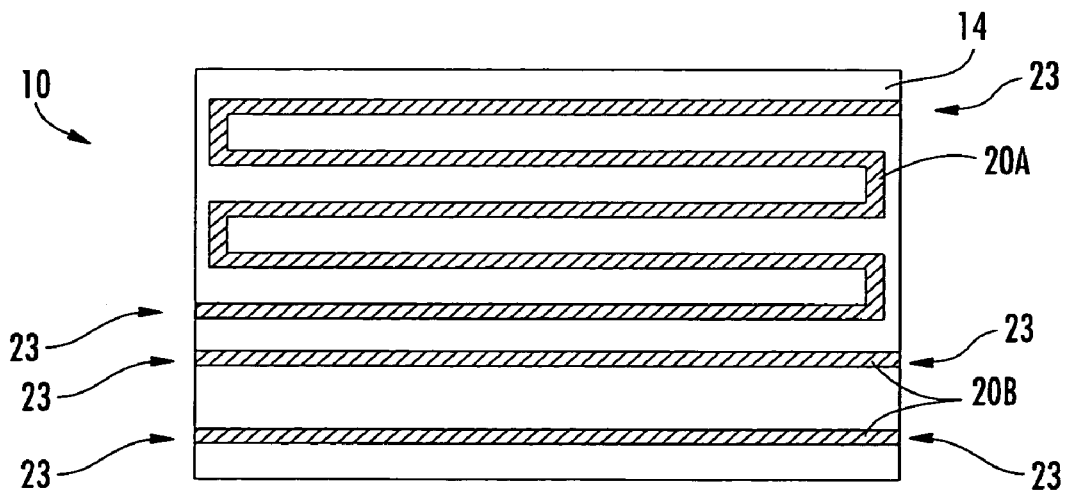
FIG. 4H is a cross-sectional view of a third arrangement of a plurality of wear conductors in the component according to aspects of the invention, viewed from line 4-4 in FIG. 1.

In other embodiments, there can be a plurality of wear conductors 20; that is, there can be at least two wear conductors 20. The two or more wear conductors 20 can be embedded in the component 10 at substantially the same depth from the exposed surface 22. The wear conductors 20 can be substantially parallel, as shown in FIG. 4F. In such case, the wear conductors 20 can be substantially equally spaced, or they can be spaced at regular or irregular intervals. In some instances, at least one of the wear conductors 20 can be non-parallel to the other wear conductors 20. At least one of the wear conductors 20 can be substantially serpentine, including in any of the manners as discussed above. There can also be combinations of any of these arrangements. For example, FIG. 4H shows an embodiment in which one wear conductor 20A is arranged in a substantially serpentine arrangement while other wear conductors 20B are provided in a substantially straight arrangement.

It should be noted that the plurality of wear conductors 20 can be electrically insulated from each other. Alternatively, at least two of the plurality of wear conductors 20 can be electrically connected. In one embodiment, the ends of the plurality of wear conductors 20 can be electrically connected so that the conductors 20 are connected in parallel, as shown in FIG. 4G. In any of the above arrangements, each of the conductors 20 can have a pair of ends. At least one end of the conductors 20 can extend in the component 10 to a connection location 23 where they can exit the component 10.

Figure 3:
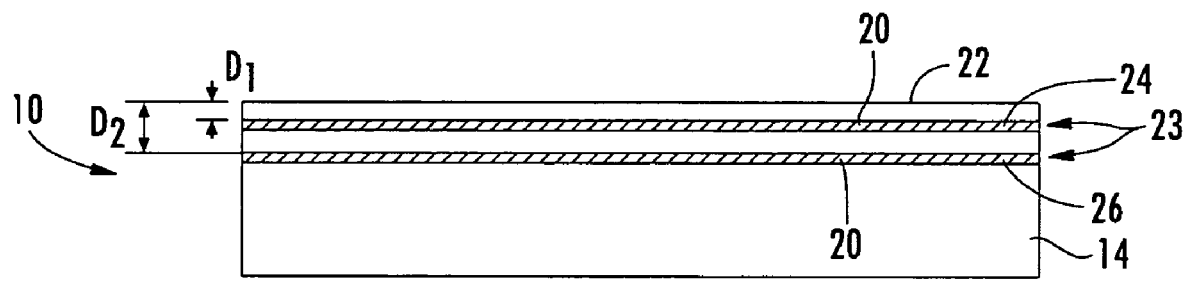
FIG. 3 is a cross-sectional elevational view of a component having wear conductors embedded at multiple levels therein according to aspects of the invention.

The wear conductors 20 can also be embedded at various depths in the component 10. One possible multi-level arrangement is shown in FIG. 3. As shown, a first layer 24 of wear conductors 20 can be embedded within the component 10 at a first depth D1 relative to the surface 18 of the component 10, and a second layer 26 of wear conductors 20 can be embedded within the component 10 at a second depth D2. While FIG. 3 shows a component 10 with two layers of wear conductors 20, it will be understood that aspects of the invention are not limited to any particular number of layers. The first and second layers 24, 26 of wear conductors 20 can be insulated from each other.

The quantity and arrangement of the wear conductors 20 in the first layer 24 can be substantially identical to or different from the quantity and arrangement of wear conductors 20 in the second layer 26. Further, the first and second layers 24, 26 of wear conductors 20 can have substantially identical areas of coverage on the component 10. However, it may be possible for the conductors 20 at one depth to have greater coverage than the conductors 20 at a different depth from the surface 18. Thus, the first and second layers 24, 26 of wear conductor 20 can also have overlapping or non-overlapping areas of coverage. The at least two layers of wear conductors 20 can be substantially parallel to each other, or at least one layer of wear conductors 20 can be non-parallel to the other layers.

The size and material of the wear conductors 20 can be selected so as not to adversely affect the performance and integrity of the component 10. In one embodiment, the wear conductors 20 can be made of one of copper, silver, platinum and alloys, just to name a few possibilities. The wear conductors 20 can also be made of other materials including conductive ceramics or conductive ceramic matrix composites. Ideally, the coefficient of thermal expansion of the wear conductors 20 substantially matches the coefficient of thermal expansion of the material in which the wear conductors 20 are embedded. The wear conductors 20 can have any cross-sectional shape. For instance, the wear conductors 20 can be circular, semi-circular, square or rectangular, just to name a few possibilities.

The wear conductors 20 may or may not be insulated from the surrounding environment. For instance, when the base material 14 or the coating 16 is an electrically insulating material and the wear conductors 20 are embedded therein, the wear conductors 20 can be provided bare. When the conductors 20 are provided on or embedded within a base material 14, coating 16 or bond coat that is conductive, the wear conductors 20 can be coated with a layer of insulating material 28. The insulating material 28 can completely surround the conductors 20, can be applied on one side of the conductors 20 or can otherwise be provided on the conductors 20 as needed to separate the conductors 20 from the neighboring conductive material.

It should be noted that the wear conductors 20 can be embedded within the component 10 in various ways. For example, the wear conductors 20 can be deposited on the substrate surface using a thermal spray process, such by micro-plasma spray. Alternatively, the wear conductors 20 can be formed in a manner similar to a microchip. In such case, the substrate surface can be oxidized or anodized to insulate it from the wear conductor 20. The conductors may be formed using physical vapor deposition (such as sputtering), chemical vapor deposition (CVD), metal oxide chemical vapor deposition (MOCVD), thermal spray processes such as high velocity oxy fuel (HVOF), air plasma spray (APS), solution based deposition approaches such as sol-gel, solution plasma spray processes or the like. The coverage area of the wear conductors 20 can be masked off, and then the wear conductor 20 can be formed by etching away the unnecessary conductor leaving the desired wear indicator circuit.

The wear conductors 20 can also be embedded within the component 10 using an electroplating process. That is, electroplating can be used to encapsulate insulated wear conductors 20 in a metallic coating. The insulated wear conductors 20 can be held in position on a metallic substrate, so that the plating can be deposited on the substrate as well as the wear conductor 20, thereby encapsulating the insulated wear conductor 20 on the substrate surface.

In another method according to aspects of the invention, the wear conductors 20 can be entrained on a substrate surface by thermal spraying a coating material on the substrate surface and about the wear conductors 20 thereon. The wear conductors 20 can be held on the substrate surface to be coated, and then the coating can be applied over the substrate surface and the wear conductor 20. In one embodiment, a bare wear conductor 20 can be encapsulated in a ceramic insulating wear coating. In another embodiment, an insulated wear conductor 20 can be encapsulated in a metallic wear coating. The coating can be built up to the desired thickness.

In one embodiment, the wear conductors 20 can be applied as a conductive film. For instance, an insulating coating can be applied to the base material of the component. The insulating coating can be applied in multiple layers. A conductive film can be applied as an intermediate layer between two successive layers of insulating coating. That is, the conductive film or layer can applied to the surface of a layer of insulating film. After the conductive film is applied on top of this layer of insulating film, another insulating layer can be applied on the conductive film and the previous layer of insulating material. The insulating material can also be a wear resistant material. If the insulating material is not wear resistant, a wear resistant material can be applied over the outermost layer of insulating material. The coating layers and the conductive film can be applied by thermal spray, painting or other conventional processes.

In addition to the above methods, the wear conductors 20 can be embedded within the component 10 using any of the methods or processes described in U.S. Patent Application Publication No. 2004/0202886, which is incorporated herein by reference.

Again, the above methods are intended to be examples of the various ways in which wear conductors 20 can be embedded within the component. Aspects of the invention are not limited to any particular manner of embedding the wear conductors 20 in the component 10.

Figure 5A:
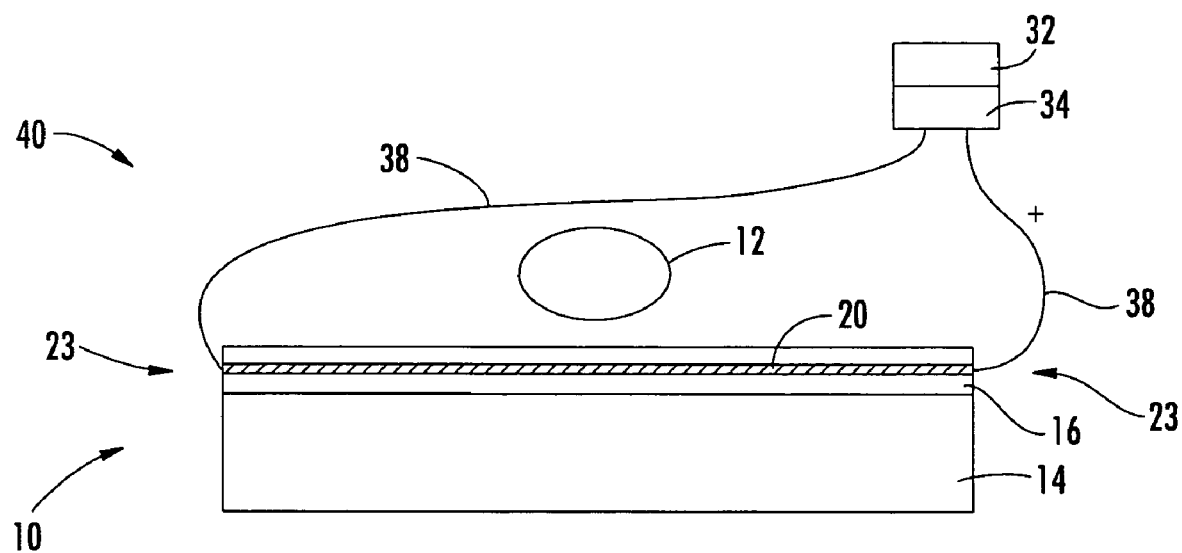
FIG. 5A is a cross-sectional elevational view of a first wear monitoring system according to aspects of the invention, wherein the component has little or no wear.
Figure 5B:
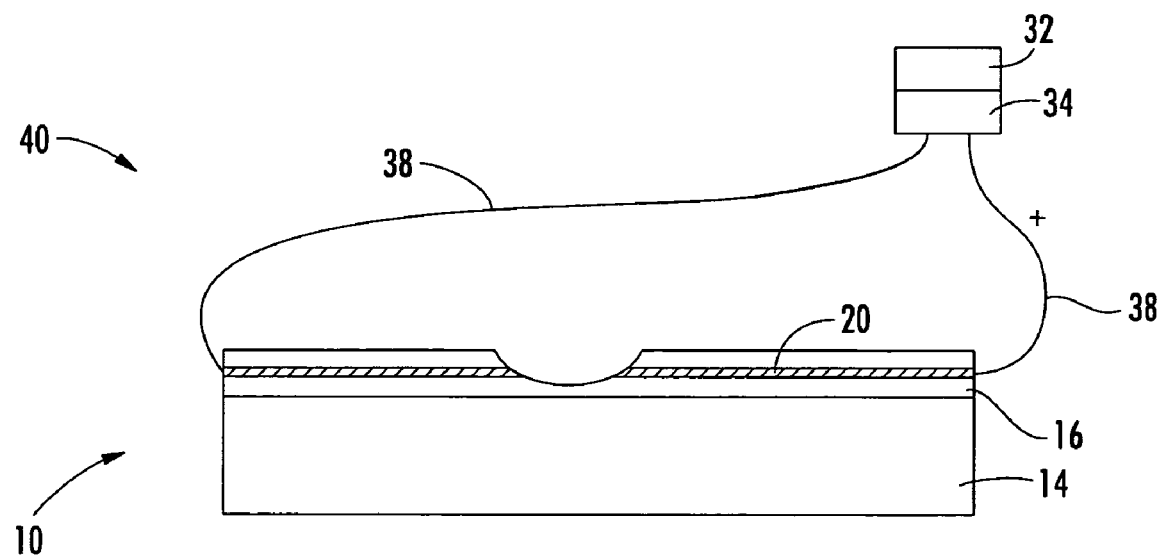
FIG. 5B is a cross-sectional elevational view of the first wear monitoring system according to aspects of the invention, wherein the wear of the component has penetrated to the wear conductor embedded therein.

Having described various possibilities for embedding wear conductors 20 in the component 10, various ways in which the wear conductors 20 can be used to monitor wear of the component 10 will now be described. A first wear monitoring system according to aspects of the invention is shown in FIGS. 5A and 5B. The system can include a measurement device 32 and a power source 34. In one embodiment, the measurement device 32 and the power source 34 can be separate devices, or they can be provided in a single device. The measurement device 32 can measure an electrical value, which can be, for example, resistance, current, voltage and/or impedance, among other things.

The wear conductors 20 can be operatively connected to the power source 34 in various ways. In the case of a single wear conductor 20, each end of the wear conductor 20 can be operatively connected to the power source 34, such as by conductors 38, to form an electrical circuit 40. The conductors 38 can operatively connect to the wear conductors 20 at the connection location 23. It will be understood that the phrase "end of the wear conductor" is not limited to the actual end of the wear conductor 20 but also includes portions of the wear conductor 20 near the actual end. When a plurality of wear conductors 20 are embedded in the component 10, each individual wear conductor 20 can be operatively connected to the power source 34 to form a plurality of isolated circuits 40. Alternatively, the plurality of wear conductors 20 can be operatively connected to the power source 34 so as to form a single circuit 40. There are various manners of forming a single circuit 40 from a plurality of wear conductors 20. For instance, in the context of the arrangement of wear conductors 20 in FIG. 4D, the plurality of wear conductors 20 can be electrically connected outside of the component 10 for operative connection to the power source 34. Alternatively, the plurality of wear conductors 20 can be electrically connected within the component 10, as shown in FIG. 4E. In such case, the wear conductors 20 can be operatively connected to the power source 34 at the connection locations 23.

Whatever the arrangement, it may be necessary to protect the connection between the wear conductors 20 and the conductors 38 from the operational environment of the component 10. To that end, the connection can be made away from the area of contact between the first and second components 10, 12. Alternatively, the connection can be shielded by, for example, a housing (not shown).

The power source 34 can supply electrical current to the wear conductor 20. In one embodiment, the power source 34 can supply direct current to the wear conductors 20. In another embodiment, the power source 34 can supply alternating current to the wear conductor 20. According to aspects of the invention, the electrical resistance of the wear conductor 20 can be measured while the component 10 is in operation or in an off-line condition. The measurement can be made on a continuous basis or according to a regular or irregular interval. The measurement device 32 can be used to selectively measure resistance and/or current. The measurement device 32 can be, for example, a voltmeter, multimeter or an ohmmeter. It should be noted that aspects of the invention include direct and indirect measurements of resistance. One manner of indirectly measuring resistance is to measure voltage across the wear conductors 20 as a substantially constant current is passed through the wear conductors 20. Using Ohm's Law, the resistance can be calculated from the measured voltage and for the known input current.

Over time, as the first and second components 10, 12 contact each other, the first component 10 can wear. If enough wear occurs, the wear conductor 20 can be reduced in cross-section; consequently, there can be a change in wear conductor resistance or amperage. Such changes can be detected by the measurement device 32. The measured change is an indication that wear has progressed to a critical point and service is required. If the wear progresses far enough, the wear conductor 20 can break, causing an open circuit, as shown in FIG. 5B. It will be appreciated that the measurement of resistance or amperage can be made across each individual wear conductor, thereby forming a series of individual circuits, or the total resistance or amperage can be measured across all of the wear conductors 20 in a single circuit 40.

Figure 6A:
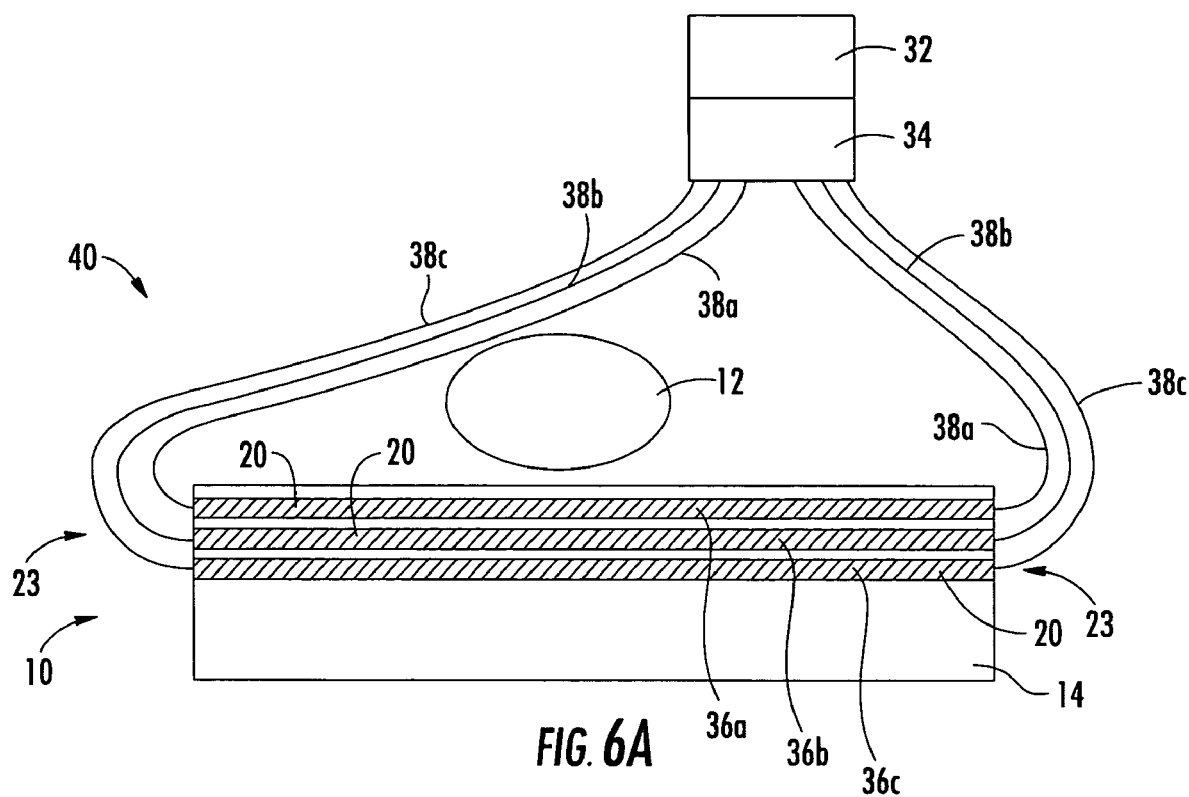
FIG. 6A is a cross-sectional elevational view of the first wear monitoring system according to aspects of the invention, wherein the component has little or no wear and showing multiple levels of embedded wear conductors.
Figure 6B:
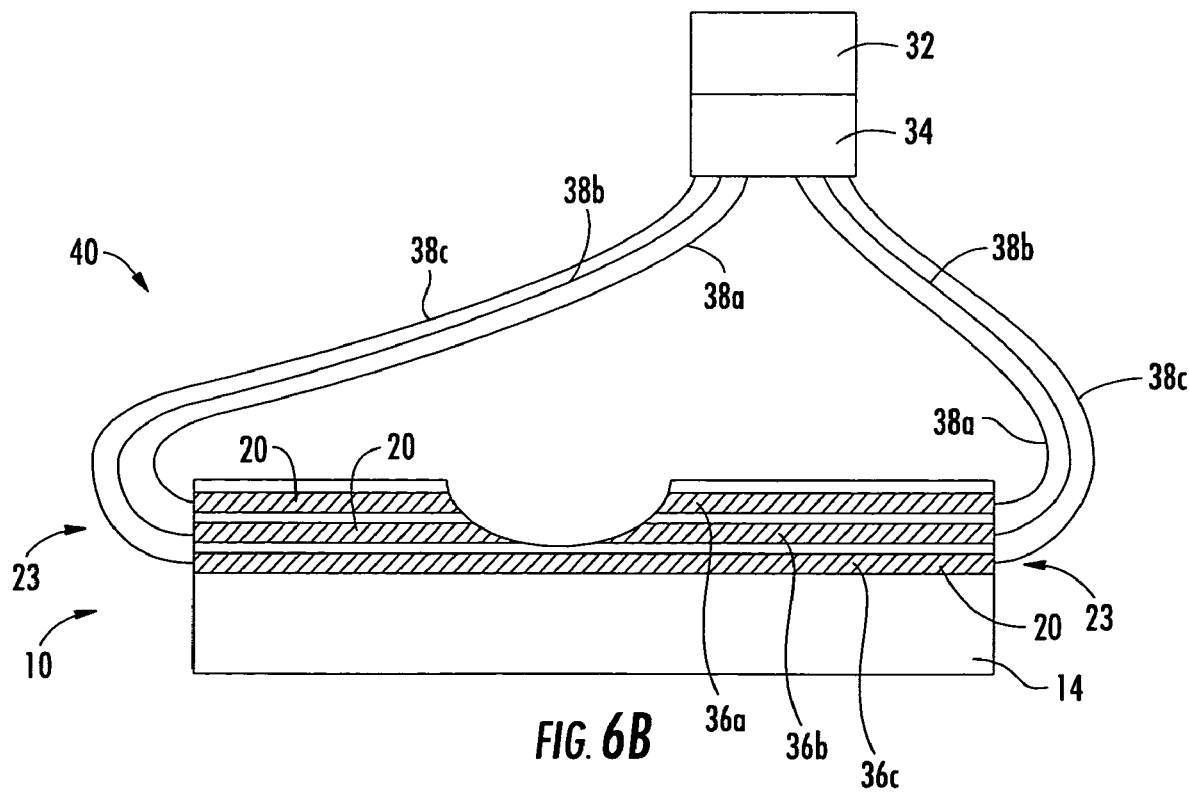
FIG. 6B is a cross-sectional elevational view of the first wear monitoring system according to aspects of the invention, wherein the wear of the component has penetrated two levels of the wear conductors embedded therein.

The above system can be configured to provide a greater degree of sensitivity as to the amount of material removed and the percentage of life remaining. To that end, multiple-layers of wear conductors 20 can be provided in the component 10 as discussed previously. FIGS. 6A and 6B show one example of such a system in which there are three layers 36a, 36b, 36c of wear conductors 20. Each layer 36a, 36b, 36c of the wear conductors 20 can be operatively connected to the power source 34 to form at least one circuit 40 for each layer 36a, 36b, 36c.

Contact between the first and second component 10, 12 can cause the first component 10 to wear. If enough wear occurs, the wear conductor 20 of the first layer 36a can be reduced in cross-section and eventually can break, as shown in FIG. 6B. As the wear progresses, similar wear can subsequently occur on the wear conductors 20 in the second and third layers 36b, 36c. Consequently, there can be a change in the resistance or amperage across the wear conductor 20. Such change can be detected by the measurement device 32, as discussed above. The measured change can alert an operator as to the depth of the wear because the wear conductors 20 were provided at particular depths in the component 10. Again, it will be appreciated that, for a multi-layer system, resistance or amperage can be measured in several ways. In one embodiment, each layer 36a, 36b, 36c can be separately connected to the power source 34 by, for example, respective conductors 38a, 38b, 38c, as shown in FIG. 6A. As a result, a plurality of individual circuits 40 can be formed. In such case, the system can examine the resistance or amperage of each of the individual circuits 40. Alternatively, the measurement can be across all of the layers 36a, 36b, 36c as a whole to form a single circuit (such an arrangement is not shown). In such case, the system can examine the change in total resistance or amperage. Because multiple layers of wear conductors 20 are provided, it may also be possible to determine the rate of wear by monitoring the changes in resistance.

Figure 7A:
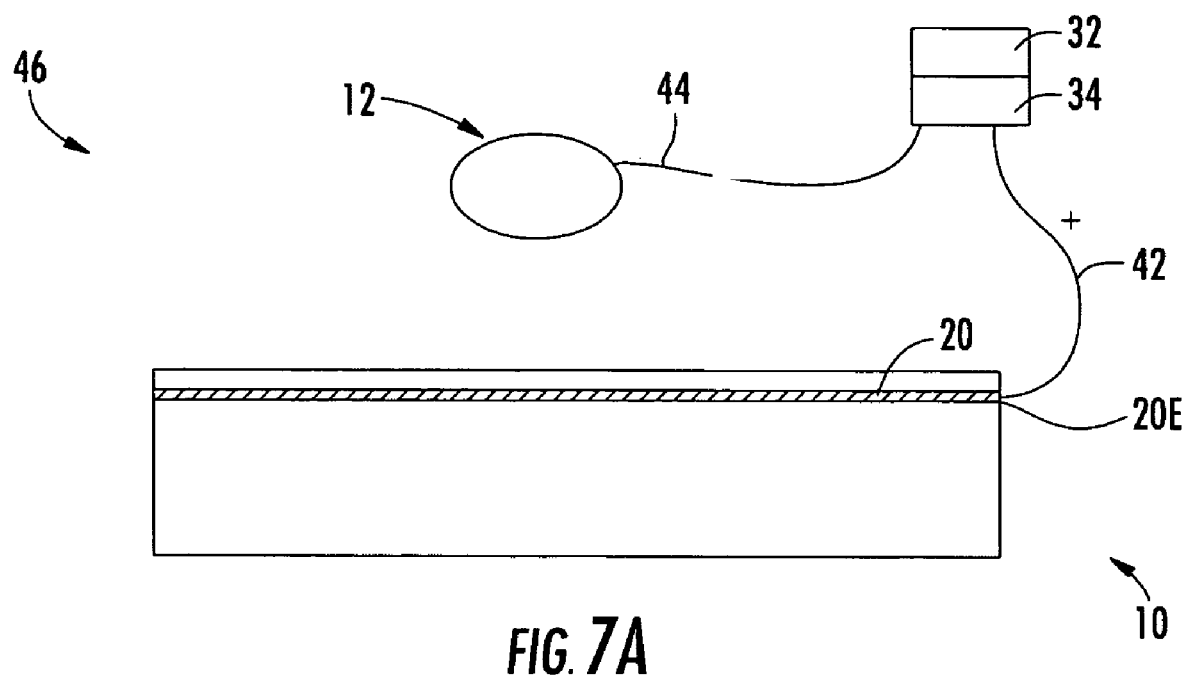
FIG. 7A is a cross-sectional elevational view of a second wear monitoring system according to aspects of the invention, wherein the component has little or no wear.
Figure 7B:
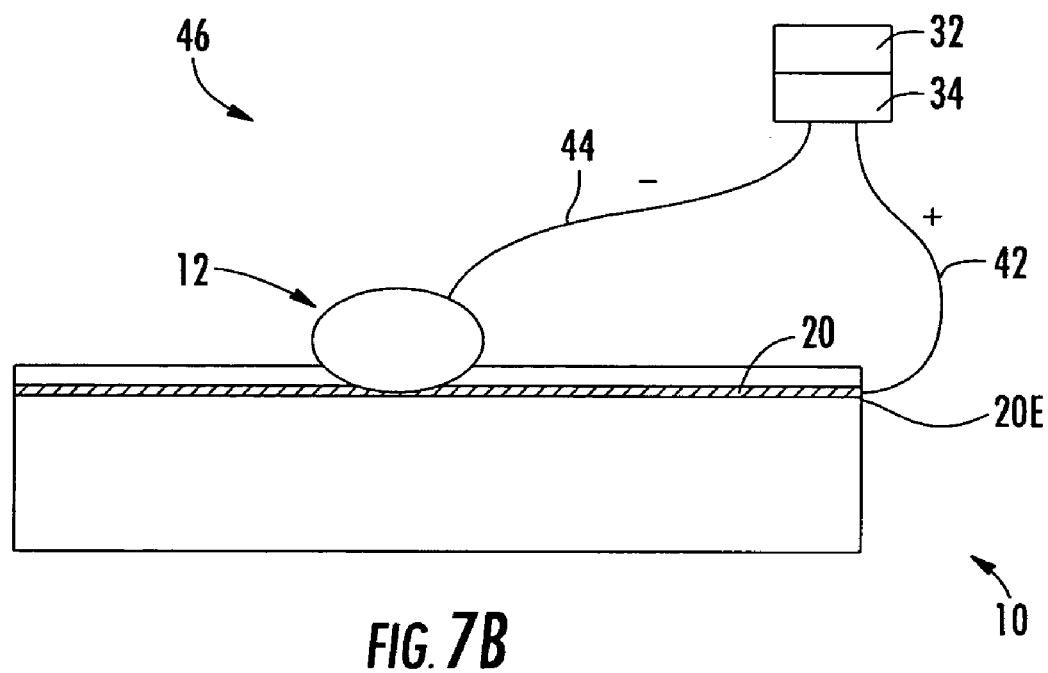
FIG. 7B is a cross-sectional elevational view of the second wear monitoring system according to aspects of the invention, wherein the wear of the component has penetrated to the wear conductor embedded therein.

Another wear monitoring system according to aspects of the invention is shown in FIGS. 7A and 7B. As shown, the power source 34 can be operatively connected to one end 20E of the wear conductor 20 by, for example, a conductor 42. Instead of being connected to the other end of the wear conductor, the power source 34 can be operatively connected to the second component 12. Such an arrangement is well suited for instances in which the portion of the second component 12 that contacts the first component 10 is metallic or is otherwise conductive. As a result of the arrangement, an incomplete circuit 46 is formed.

While in use, the first and second components 10, 12 can contact each other, causing the first component 10 to wear. Eventually, the first component 10 can wear to the point that the wear conductor 20 is exposed. It will be appreciated that, when the exposed wear conductor 20 and the second component 12 come into contact, the circuit 46 is completed. Thus, current can flow across at least a portion of the wear conductor 20. Such a change in condition can be registered by the measurement device 32. Thus, a user will be alerted that the wear of the first component 10 has progressed to a certain point and that service may be required.

Figure 8A:
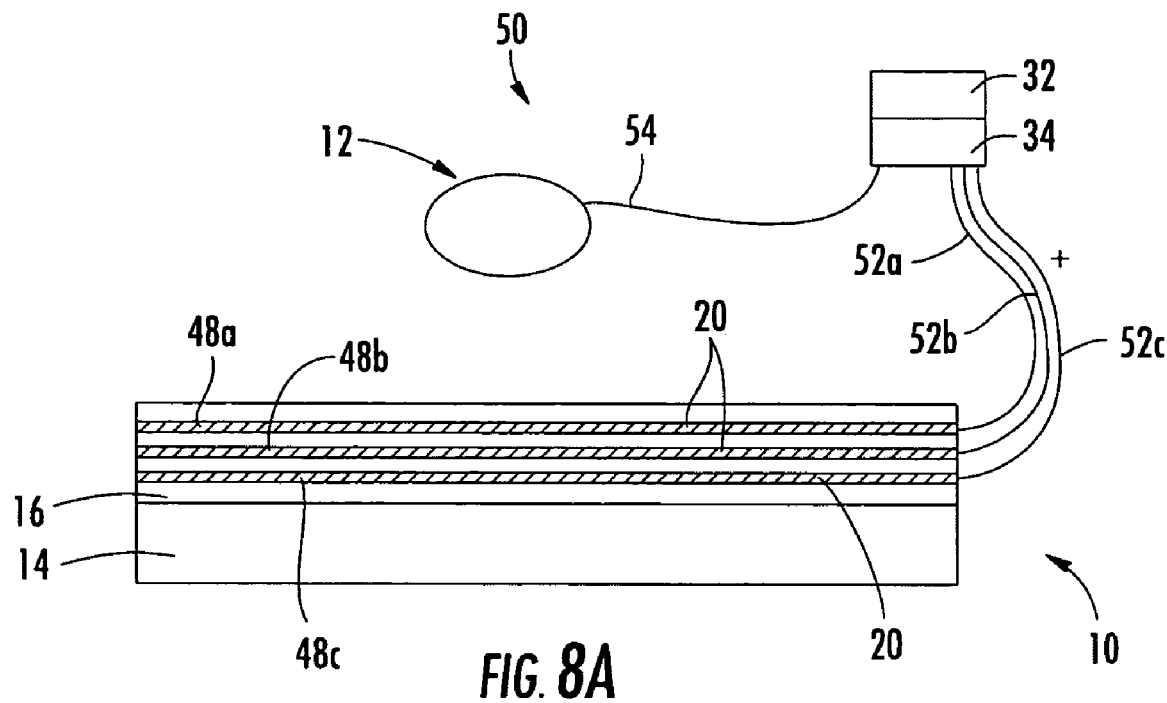
FIG. 8A is a cross-sectional elevational view of the second wear monitoring system according to aspects of the invention, wherein the component has little or no wear and showing multiple levels of embedded wear conductors.
Figure 8B:
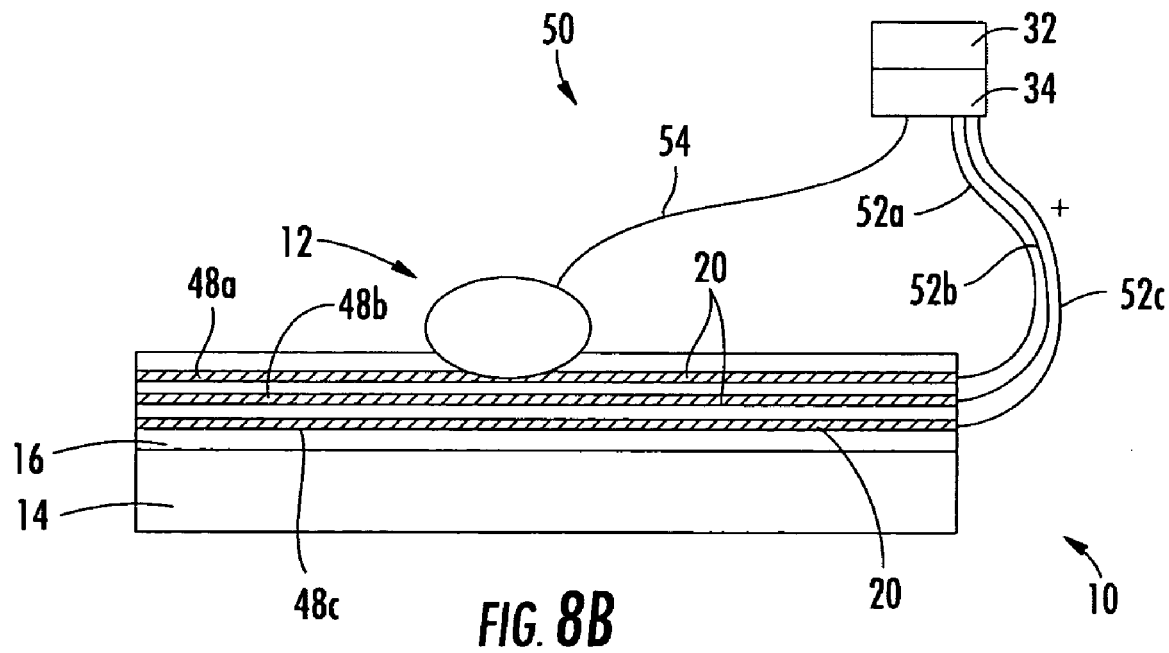
FIG. 8B is a cross-sectional elevational view of the second wear monitoring system according to aspects of the invention, wherein the wear of the component has penetrated two levels of the wear conductors embedded therein.

It will be appreciated that the above system can be configured with multiple layers of wear conductors 20, as shown in FIGS. 8A and 8B. Thus, the system can provide more information concerning the amount of wear of the component 10, the percentage of life remaining and the rate of wear. In the embodiment shown, there can be three layers 48a, 48b, 48c of wear conductors 20. One end of each layer 48a, 48b, 48c can be operatively connected to the power source 34 to form an incomplete circuit 50 for each layer 48a, 48b, 48c.

The component 10 can wear due to contact between the first and second components 10, 12. If enough wear occurs, the wear conductor 20 of the first layer 48a can become exposed and can come into contact with the second component 12, as shown in FIG. 8B. If the wear continues, the second component 12 can come into contact with the conductors 20 in the second and third layers 48b, 48c. When the second component 12 contacts any of the wear conductors 20, the circuit 50 is completed, allowing current to flow through at least a portion of the conductor 20 and the second component 12. As the second component 12 completes one or more circuits 50 with each of individual layers 48a, 48b, 48c, the measurement device 32 can detect such changes as a change in resistance or amperage.

As noted earlier, there are several ways to measure resistance or amperage in a multi-layer arrangement of conductors 20. In one embodiment, each layer 48a, 48b, 48c can be separately connected to the power source 34 by, for example, respective conductors 52a, 52b, 52c, as is shown in FIG. 8A. At least a portion of the second component 12 can be operatively connected to the power source 34, such as by conductor 54. As a result, a plurality of individual open circuits 50 can be formed. In such case, the measurement device 32 can detect changes in the resistance or amperage of each of the individual circuits 50. Alternatively, the measurement can be across all of the layers 48a, 48b, 48c to form a single open circuit (not shown). In such case, the change in total resistance or amperage can be monitored. The use of impedance can provide further information as to how deep the second component 12 has penetrated the first component 10.

According to aspects of the invention, any of the above-described systems can measure impedance instead of resistance or amperage. Impedance can be evaluated in a manner analogous to standard or complex eddy current measurements. In such case, the power source 34 can supply alternating current to the circuit. Impedance can be defined as the total opposition offered to the flow of an alternating current. Impedance can be affected by resistance, capacitance and inductance; impedance can also be influenced by the dielectric permeability of the material surrounding the circuit (here the base material 14 or the coating 16 of the component 10). Thus, as the component 10 wears during operation, changes in impedance can be expected as a result of loss of surface material. Changes in impedance can be evidenced on the measurement device 32, which can be, for example, an oscilloscope (not shown), by changes in the wave form and phase shifts. In one embodiment, any of the circuits 40, 46, 50 discussed above can be evaluated at higher frequencies, which can be from about 50 kHz to greater than about 10 MHz, for near conductor or coil behavior. Alternatively, the circuits 40, 46, 50 can be evaluated at lower frequencies, such as from about 500 Hz to about 50 kHz, for farther reaching effects. Such lower frequencies can penetrate further into the component 10 but at lower resolution.

It should be noted that in any of the embodiments discussed above, a code element (not shown) can be operatively associated with the power source 34, the measurement device 32, and/or the conductors 38 (including 38a, 38b, 38c), 42, 44, 52 (including 52a, 52b, 52c), 54. The code element can enable a clear distinction as to which circuit 40, 46, 50 has been completed, especially in cases where there are a plurality of wear conductors 20 at the same depth or at different depths. The code element can be, for example, a resistor, a capacitor or an inductor.

The foregoing description is provided in the context of various possible wear monitoring systems and methods. It will of course be understood that the invention is not limited to the specific details described herein, which are given by way of example only, and that various modifications and alterations are possible within the scope of the invention as defined in the following claims.

What is claimed is:

1. A wear monitoring system comprising:
  a first component having a surface;
  a second component;
  a first conductor embedded in the first component at a predetermined depth beneath the surface and being electrically insulated from the first component;
  a power source operatively connected to provide current to the first conductor, whereby an electrical circuit is formed; and
  a measurement device operatively positioned to measure an electrical value across at least a portion of the first conductor,
  wherein the second component contacts the surface of the first component such that at least the surface of the first component wears, whereby a user can monitor the measurement device for changes in the measured value indicating that the wear has progressed at least to the predetermined depth, wherein the current flows through the first conductor prior to the wear progressing to the predetermined depth.

2. The system of claim 1 wherein the first and second components are gas turbine engine components.

3. The system of claim 1 wherein the electrical value is one of resistance, current, voltage and impedance.

4. The system of claim 1 further including:
  a second conductor embedded in the first component at a predetermined depth beneath the surface, wherein the second conductor is operatively connected to receive current from the power source, and wherein the measurement device is operatively positioned to measure the value across at least a portion of the second conductor.

5. The system of claim 4 wherein the first and second conductors we electrically insulated from each other and are separately operatively connected to the power source, whereby two isolated circuits are formed.

6. The system of claim 4 wherein the first and second conductors are provided in the first component at substantially the same depth beneath the surface of the first component.

7. The system of claim 4 wherein the first and second conductors are electrically connected in parallel.

8. The system of claim 4 wherein the first and second conductors are provided in the first component at different depths beneath the surface of the first component.

9. The system of claim 8 wherein the first conductor and the second conductor provide at least partially overlapping areas of coverage about the first component.

10. The system of claim 1 wherein the first component includes a base material with at least one layer of a coating thereon, wherein the first conductor is embedded within the coating.

11. A wear monitoring system comprising:
  a first component having a fast surface;
  a second component having a second surface, wherein at least a portion of the second surface of the second component is conductive;
  a first conductor embedded in the first component at a predetermined depth beneath the first surface;
  a second conductor embedded in the first component at another predetermined depth beneath the first surface, and
  a power source operatively connected to the first conductor and to the conductive surface of the second component, wherein an initially open circuit is formed,
  the second surface and the first surface being in contact such that at least the fast surface wears, wherein, when the first surface is sufficiently worn such that the second surface contacts the first conductor, the circuit is completed, whereby the completion of the circuit can alert a user that the wear has progressed to at least the predetermined depth,
  wherein the second conductor is operatively connected to receive current from the power source such that an initially open circuit is formed,
  wherein when the first surface is sufficiently worn such that the second surface contacts the second conductor, the circuit is completed, whereby the completion of the circuit can alert a user that the wear has progressed to at least the another predetermined depth,
  wherein the first and second conductors are electrically insulated from each other and are separately operatively connected to the power source, whereby two isolated initially open circuits are formed, and
  wherein the first and second conductors are provided in the first component at different depths beneath the first surface of the first component.

12. The system of claim 11 further including a measurement device operatively positioned to measure at least one of resistance, current, voltage and impedance across at least a portion of the first conductor and the conductive surface of the second component, whereby changes in the measured resistance, current, voltage and impedance indicate that a predetermined amount of wear has occurred.

13. The system of claim 11 wherein the first component is a gas turbine engine component.

14. The system of claim 11 wherein the first conductor and the second conductor provide at least partially overlapping areas of coverage about the first component.

15. The system of claim 11 wherein the first and second conductors are electrically connected in parallel.

16. The system of claim 11 wherein the first component includes a base material with at least one layer of a coating thereon, wherein the first conductor is embedded within the coating.

* * * * *